United States Patent
Knox et al.

(10) Patent No.: US 6,228,599 B1
(45) Date of Patent: May 8, 2001

(54) ANTIBODY SPECIFIC FOR HOMOGALACTURONAN

(75) Inventors: John Paul Knox, Leeds; William George Tycho Willats, Ilklay, both of (GB); Jorn Dalgaard Mikkelsen, Hvidovre (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/260,527

(22) Filed: Feb. 26, 1999

(30) Foreign Application Priority Data

Dec. 24, 1998 (GB) .................................................. 9828700

(51) Int. Cl.⁷ .......................... G01N 33/53; C07K 16/00; C12P 21/08
(52) U.S. Cl. ........................ 435/7.1; 435/810; 530/387.1; 530/387.3; 530/387.5
(58) Field of Search ................. 435/7.1, 810; 530/387.1, 530/387.3, 387.5

(56) References Cited

U.S. PATENT DOCUMENTS 5,556,763 * 9/1996 Ochoa et al. .

OTHER PUBLICATIONS

Mikayama et al. PNAS 90:10056–10060, 1993.*
Liners et al. Plant Pysiol. 99:1099–1104, 1992.*
Knox et al. Planta 181:512–521, 1990.*

* cited by examiner

*Primary Examiner*—Patrick J. Nolan
*Assistant Examiner*—Gerald R. Ewoldt
(74) *Attorney, Agent, or Firm*—Knobbe, Martens, Olson & Bear, LLP

(57) ABSTRACT

Antibodies specific to pectin, specifically to homogalacuronin capable of recognizing a certain motif on the pectin structure were produced. These antibodies can be used alone or linked to a detectable moiety. They can be used in an assay or can be used to produce a food.

4 Claims, 4 Drawing Sheets

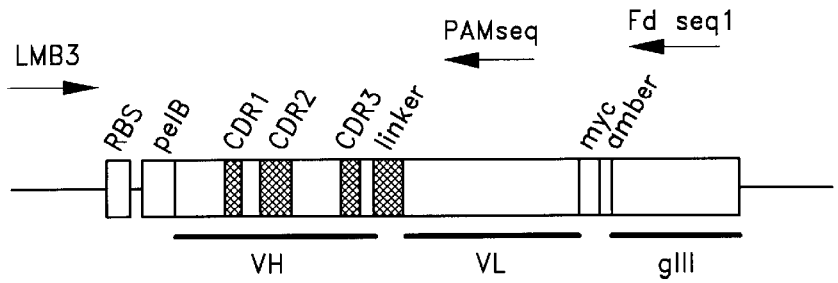

FIG. 4A

```
Pam1  MKYLLPTAAAGLLLLAAQPAMAEVQLVESGGGLVKPGGSLRLSCAASGFT
Pam2  MKYLLPTAAAGLLLLAAQPAMAQVQLQESGPGLVKPSDTLSLTCAVSGYS 51                                              100
Pam1  FSNA-WMSWVRQAPGKGLEWVGRIKSKTDGGTTDYAAPVKGRFTISRDDS
Pam2  ISSSNWWGWIRQPPGKGLEWIGYI...YYSGSTYYNPSLKSRVTMSVDTS 101                                             150
Pam1  KNTLYLQMNSLKTEDTAVYYCARKWRKALRWGQGTLVTVSR
Pam2  KNQFSLKLSSVTAVDTAVYYCARFHPRVYDWGQGTLVTVSR 151                                             200
Pam1         ELTQDPAVSVALGQTVRITCQGDSLRSYYASWYQQKPGQAPVL
Pam2         ELTQDPAVSVALGQTVRITCQGDSLRSYYASWYQQKPGQAPVL 201                                             250
Pam1  VIYGKNNRPSGIPDRFSGSSSGNTASLTTTGAQAEDEADYYCNSRDSSGN
Pam2  VIYGKNNRPSGIPDRFSGSSSGNTASLTITGAQAEDEADYYCNSRDSSGN 251                          285
Pam1  HVVFGGGTKLTVLGAAAEQKLISEEDLN GAA (E) T
Pam2  HVVFGGGTKLTVLGAAAEQKLISEEDLN GAA (E) T
```

FIG. 4B

SEQUENCE LISTING

```
<160> NUMBER OF SEQ ID NOS: 7

<210> SEQ ID NO 1
<211> LENGTH: 280
<212> TYPE: PRT
<213> ORGANISM: UNKNOWN
<220> FEATURE:
<223> OTHER INFORMATION: Anti-homogalacturonan specific antibodies from
      a phage display library known as the Synthetic scFv Library (#1)
      from the Centre for Protein Engineering, MRC Centre, Cambridge,
      UK.

<400> SEQUENCE: 1

Met Lys Tyr Leu Leu Pro Thr Ala Ala Ala Gly Leu Leu Leu Ala
1               5                   10                  15

Ala Gln Pro Ala Met Ala Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asn Ala Trp Met Ser Trp Val Arg Gln Ala Pro Gly
    50                  55                  60

Lys Gly Leu Glu Trp Val Gly Arg Ile Lys Ser Lys Thr Asp Gly Gly
65                  70                  75                  80
```

```
Thr Thr Asp Tyr Ala Ala Pro Val Lys Gly Arg Phe Thr Ile Ser Arg
            85                  90                  95

Asp Ser Lys Asn Thr Leu Tyr Leu Gln Met Asn Ser Leu Lys Thr
Asp         100                 105                 110

Glu Asp Thr Ala Val Tyr Tyr Cys Ala Arg Lys Trp Arg Lys Ala Leu
        115                 120                 125

Arg Trp Gly Gln Gly Thr Leu Val Thr Val Ser Arg Gly Gly Gly
    130                 135                 140

Ser Gly Gly Gly Ser Gly Gly Gly Ser Ser Glu Leu Thr Gln
145             150              155                 160

Asp Pro Ala Val Ser Val Ala Leu Gly Gln Thr Val Arg Ile Thr Cys
            165                 170                 175

Gln Gly Asp Ser Leu Arg Ser Tyr Tyr Ala Ser Trp Tyr Gln Gln Lys
        180                 185                 190

Pro Gly Gln Ala Pro Val Leu Val Ile Tyr Gly Lys Asn Asn Arg Pro
        195                 200                 205

Ser Gly Ile Pro Asp Arg Phe Ser Gly Ser Ser Ser Gly Asn Thr Ala
        210                 215                 220

Ser Leu Thr Ile Thr Gly Ala Gln Ala Glu Asp Ala Asp Tyr Tyr
225             230                 235                 240

Cys Asn Ser Arg Asp Ser Ser Gly Asn His Val Val Phe Gly Gly Gly
            245                 250                 255

Thr Lys Leu Thr Val Leu Gly Ala Ala Ala Glu Gln Lys Leu Ile Ser
            260                 265                 270

Glu Glu Asp Leu Asn Gly Ala Ala
        275                 280

<210> SEQ ID NO 2
<211> LENGTH: 831
<212> TYPE: DNA
<213> ORGANISM: UNKNOWN
<220> FEATURE:
<223> OTHER INFORMATION: anti-homogalacturonan specific antibody from a
      naive phage display library known as the Synthetic
      scFv Library (#1) from the Centre for Protein
      Engineering, MRC Centre, Cambridge, UK

<400> SEQUENCE: 2
atgaaatacc tattgcctac ggcagccgct ggattgttat tactcgcggc ccagccggcc    60
atggccgagg tgcagctggt ggagtctggg ggaggcttgg taaagcctgg ggggtccctt   120
agactctcct gtgcagcctc tggattcact ttcagtaacg cctggatgag ctgggtccgc   180
caggctccag gaaggggct ggagtgggtt ggccgtatta aaagcaaaac tgatggtggg   240
acaacagact acgctgcacc cgtgaaaggc agattcacca tctcaagaga tgattcaaaa   300
aacacgctgt atctgcaaat gaacagcctg aaaaccgagg acacggccgt gtattactgt   360
gcaagaaagt ggaggaaggc gcttcggtgg ggccaaggta ccctggtcac cgtgtcgaga   420
ggtggaggcg gttcaggcgg aggtggctct ggcggtggcg gatcgtctga gctgactcag   480
gaccctgctg tgtctgtggc cttgggacag acagtcagga tcacatgcca aggagacagc   540
ctcagaagct attatgcaag ctggtaccag cagaagccag acaggcccc tgtacttgtc   600 atctatggta aaaacaaccg gccctcaggg atcccagacc gattctctgg ctccagctca   660
ggaaacacag cttccttgac catcactggg gctcaggcgg aagatgaggc tgactattac   720
tgtaactccc gggacagcag tggtaaccat gtggtattcg gcgagggac caagctgacc   780 gtcctaggtg cggccgcaga acaaaaactc atctcagaag aggatctgaa t            831
```

<210> SEQ ID NO 3
<211> LENGTH: 278
<212> TYPE: PRT
<213> ORGANISM: UNKNOWN
<220> FEATURE:
<223> OTHER INFORMATION: Anti-homogalacturonan specific antibodies selected from a naive phage display library known as the Synthetic scFv Library (#1) from the Centre for Protein Engineering, MRC Centre, Cambridge, UK

<400> SEQUENCE: 3

```
Met Lys Tyr Leu Leu Pro Thr Ala Ala Gly Leu Leu Leu Ala
 1               5                  10                  15

Ala Gln Pro Ala Met Ala Gln Val Gln Leu Gln Glu Ser Gly Pro Gly
            20                  25                  30

Leu Val Lys Pro Ser Asp Thr Leu Ser Leu Thr Cys Ala Val Ser Gly
        35                  40                  45

Tyr Ser Ile Ser Ser Ser Asn Trp Trp Gly Trp Ile Arg Gln Pro Pro
    50                  55                  60

Gly Lys Gly Leu Glu Trp Ile Gly Tyr Ile Tyr Tyr Ser Gly Ser Thr
65                  70                  75                  80

Tyr Tyr Asn Pro Ser Leu Lys Ser Arg Val Thr Met Ser Val Asp Thr
                85                  90                  95

Ser Lys Asn Gln Phe Ser Leu Lys Leu Ser Ser Val Thr Ala Val Asp
            100                 105                 110

Thr Ala Val Tyr Tyr Cys Ala Arg Phe His Pro Arg Val Tyr Asp Trp
        115                 120                 125

Gly Gln Gly Thr Leu Val Thr Val Ser Arg Gly Gly Gly Gly Ser Gly
    130                 135                 140

Gly Gly Ser Gly Gly Gly Ser Ser Glu Leu Thr Gln Asp Pro
145                 150                 155                 160

Ala Val Ser Val Ala Leu Gly Gln Thr Val Arg Ile Thr Cys Gln Gly
                165                 170                 175

Asp Ser Leu Arg Ser Tyr Tyr Ala Ser Trp Tyr Gln Gln Lys Pro Gly
            180                 185                 190

Gln Ala Pro Val Leu Val Ile Tyr Gly Lys Asn Asn Arg Pro Ser Gly
        195                 200                 205

Ile Pro Asp Arg Phe Ser Gly Ser Ser Gly Asn Thr Ala Ser Leu
    210                 215                 220

Thr Ile Thr Gly Ala Gln Ala Glu Asp Glu Ala Asp Tyr Tyr Cys Asn
225                 230                 235                 240

Ser Arg Asp Ser Ser Gly Asn His Val Val Phe Gly Gly Gly Thr Lys
                245                 250                 255

Leu Thr Val Leu Gly Ala Ala Ala Glu Gln Lys Leu Ile Ser Glu Glu
            260                 265                 270

Asp Leu Asn Gly Ala Ala
        275
```

<210> SEQ ID NO 4
<211> LENGTH: 840
<212> TYPE: DNA
<213> ORGANISM: UNKNOWN
<220> FEATURE:
<223> OTHER INFORMATION: Anti-homogalacturonan specific antibodies selected from a naive phage display library known as the Synthetic scFv Library (#1) from the Centre for Protein Engineering, MRC Centre, Cambridge, UK -continued

```
<400> SEQUENCE: 4
atgaaatacc tattgcctac ggcagccgct ggattgttat tactcgcggc ccagccggcc      60
atggcccagg tgcagctgca ggagtcgggc ccaggactgg tgaagccttc ggacaccctg     120
tccctcacct gcgctgtctc tggttactcc atcagcagta gtaactggtg gggctggatc     180
cggcagcccc cagggaaggg actggagtgg attgggtaca tctattatag tgggagcacc     240
tactacaacc cgtccctcaa gagtcgagtc accatgtcag tagacacgtc caagaaccag     300
ttctccctga agctgagctc tgtgaccgcc gtggacacgg ccgtgtatta ctgtgcaaga     360
tttcatccga gggtgtatga ttggggccaa ggtaccctgg tcaccgtgtc gagaggtgga     420
ggcggttcag gcggaggtgg ctctggcggt ggcggatcgt ctgagctgac tcaggaccct     480
gctgtgtctg tggccttggg acagacagtc aggatcacat gccaaggaga cagcctcaga     540
agctattatg caagctggta ccagcagaag ccaggacagg cccctgtact tgtcatctat     600
ggtaaaaaca accggccctc agggatccca gaccgattct ctggctccag ctcaggaaac     660
acagcttcct tgaccatcac tggggctcag gcggaagatg aggctgacta ttactgtaac     720
tcccgggaca gcagtggtaa ccatgtggta ttcggcggag ggaccaagct gaccgtccta     780
ggtgcggccg cagaacaaaa actcatctca gaagaggatc tgaatggggc cgcatagact     840

<210> SEQ ID NO 5
<211> LENGTH: 17
<212> TYPE: DNA
<213> ORGANISM: Artificial Sequence
<220> FEATURE:
<223> OTHER INFORMATION: sequencing primer sequence LMB3

<400> SEQUENCE: 5
caggaaacag ctatgac                                                     17

<210> SEQ ID NO 6
<211> LENGTH: 17
<212> TYPE: DNA
<213> ORGANISM: Artificial Sequence
<220> FEATURE:
<223> OTHER INFORMATION: Sequencing primer sequence fd-SEQ1

<400> SEQUENCE: 6
gaattttctg tatgagg                                                     17

<210> SEQ ID NO 7
<211> LENGTH: 17
<212> TYPE: DNA
<213> ORGANISM: Artificial Sequence
<220> FEATURE:
<223> OTHER INFORMATION: Sequencing primer sequence PAM seq1

<400> SEQUENCE: 7
tgaggctgtc tccttgg                                                     17
```

ANTIBODY SPECIFIC FOR HOMOGALACTURONAN

FIELD OF THE INVENTION

The present invention relates to an antibody. In particular, the present invention relates to an antibody that is capable of recognizing a certain motif on a pectin structure.

BACKGROUND OF THE INVENTION

Primary plant cell walls are fibrous composite structures consisting of cellulose microfibrils embedded in a heterogeneous polymer matrix of which a major constituent is pectin. In addition to a directly structural role, the pectic network provides a dynamic operating environment within the primary cell wall matrix and is involved in cell adhesion, regulation of cell wall porosity, cell wall extensibility and ionic status.

Pectins are immensely complex not only in their composition but also in their linkages and in their intermolecular bonds. In most cell types they principally comprise the following three types of polysaccharides: homogalacturonan (HG), rhamnogalacturonan I (RGI) and rhamnogalacturonan II (RGI).

The organization, integration and precise structures and functions of these pectic polysaccharides within primary cell walls is still not fully understood.

However, it is known that HG can contain long interrupted sequences of contiguous ($\alpha$-1,4-linked-GalA residues (known as HG blocks) that may be interspersed with rhamnose residues either occasionally or as repeating GalA-Rha structures. In vivo, HG is thought to be synthesized in a form with extensive methyl-esterification at the C-6 carboxyl position.

It is also thought that the controlled de-esterification of pectin by pectin methyl esterases within the cell wall influences pectic gel formation, principally by means of the formation of calcium bridges between stretches of de-esterified HG blocks at 'junction zones'. Furthermore, de-esterification also influences the susceptibility of HG to hydrolytic and degradative enzymes such as polygalacturonases.

The mechanical properties of pectin gels are important both structurally, in that they contribute to the resisting of turgor pressure, and physiologically in that they determine the porosity of the cell wall. It is thought that cell wall porosity may regulate, by physical exclusion, the access of cell wall modifying enzymes to polymer substrates and so influence changes in cell wall architecture. HG is also an important source of biologically active oligogalacturonides (OGAs) that appear to have roles as signalling molecules in both plant development and defence.

Thus, HG is a multi-functional pectic polysaccharide of primary cell walls involved in calcium cross-linking and gel formation, the regulation of the ionic status and porosity of the primary cell wall matrix and is a source of oligosaccharins functioning in plant development and defence.

In addition to the above commentary, it is known that pectin comprises highly branched regions with an almost alternating rhamno-galacturonan chain. These highly branched regions may also contain other sugar units (such as D-galactose, L-arabinose and xylose) attached by glycosidic linkages to the C3 or C4 atoms of the rhamnose units or the C2 or C3 atoms of the galacturonic acid units. The long chains of ($\alpha$-1-4 linked galacturonic acid residues are commonly referred to as "smooth" regions, whereas the highly branched regions are commonly referred to as the "hairy regions".

As indicated above, some of the carboxyl groups of the galacturonic residues are esterified (e.g. the carboxyl groups are methylated). Typically esterification of the carboxyl groups occurs after polymerization of the galacturonic acid residues. However, it is extremely rare for all of the carboxyl groups to be esterified (e.g. methylated).

Usually, the degree of esterification ("DE") will vary from 0–90%. If 50% or more of the carboxyl groups are esterified then the resultant pectin is referred to as a "high ester pectin" ("HE pectin" for short) or a "high methoxyl pectin". If less than 50% of the carboxyl groups are esterified then the resultant pectin is referred to as a "low ester pectin" ("LE pectin" for short) or a "low methoxyl pectin". If 50% of the carboxyl groups are esterified then the resultant pectin is referred to as a "medium ester pectin" ("ME pectin" for short) or a "medium methoxyl pectin". If the pectin does not contain any—or only a few—esterified groups it is usually referred to as pectic acid.

A Protocol for determining the degree of esterification of the PME substrate may be found on page 58 of WO-A-97/03574. For ease of reference, this Protocol is recited below.

DEGREE OF ESTERIFICATION (%DE)

To 50 ml of a 60% isopropanol and a 5% HC1 solution is added 2.5 g pectin sample and stirred for 10 min. The pectin solution is filtered through a glass filter and washed with 15 ml 60 % isopropanol/5% HC1 solution 6 times followed by further washes with 60% isopropanol until the filtrate is free of chlorides. The filtrate is dried overnight at 80° C.

20.0 ml 0.5 N NaOH and 20.0 ml 0.5 N HC1 is combined in a conical flask and 2 drops of phenolphthalein is added. This is titrated with 0.1 N NaOH until a permanent color change is obtained. The 0.5 N HC1 should be slightly stronger than the 0.5N NaOH. The added volume of 0.1 N NaOH is noted as V0.

0.5 g of the dried pectin sample (the filtrate) is measured into a conical flask and the sample is moistened with 96% ethanol. 100 ml of recently boiled and cooled destined water is added and the resulting solution stirred until the pectin is completely dissolved. Then 5 drops of phenolphthalein are added and the solution titrated with 0.1 N NaOH (until a change in color and pH is 8.5). The amount of 0.1 N NaOH used here is noted as V1. 20.0 ml of 0.5 N NaOH is added and the flask shaken vigously, and then allowed to stand for 15 min. 20.0 ml of 0.5 N HC1 is added and the flask is shaken until the pink color disappears. 3 drops of phenolphthalein are then added and then the resultant solution is titrated with 0.1 N NaOH. The volume 0.1 N NaOH used is noted as V2.

The degree of esterification (% DE: % of total carboxy groups) is calculated as follows:

$$\% DE = \frac{V2 - V0}{V1 + (V2 - V0)}$$

As indicated above, the structure of the pectin, in particular the degree of esterification (e.g. methylation), dictates many of the resultant physical and/or chemical properties of the pectin. For example, pectin gelation depends on the chemical nature of the pectin, especially the degree of esterification. In addition, however, pectin gelation also depends on the soluble-solids content, the pH and calcium ion concentration. With respect to the latter, it is believed that the calcium ions form complexes with free carboxyl groups, particularly those on a LE pectin.

A Protocol for determining calcium sensitivity may be found on page 57 of WO-A-97/03574. For ease of reference, this Protocol is recited below.

CALCIUM SENSITIVITY INDEX (CF)

Calcium sensitivity is measured as the viscosity of a pectin dissolved in a solution with 57.6 mg calcium/g pectin divided by the viscosity of exactly the same amount of pectin in solution, but without added calcium. A calcium insensitive pectin has a CF value of 1.

4.2 g pectin sample is dissolved in 550 ml hot water with efficient stirring. The solution is cooled to about 20ø C. and the pH adjusted to 1.5 with IN HC1. The pectin solution is adjusted to 700 ml with water and stirred. 145 g of this solution is measured individually into 4 viscosity glasses. 10 ml water is added to two of the glasses (double determinations) and 10 ml of a 250 mM CaC12 solution is added to the other two glasses under stirring.

50 ml of an acetate buffer (0.5 M, pH about 4.6) is added to all four viscosity glasses under efficient magnetic stirring, thereby bringing the pH of the pectin solution up over pH 4.0. The magnets are removed and the glasses left overnight at 20°C. The viscosities are measured the next day with a Brookfield viscometer. The calcium sensitivity index is calculated as follows:

$$CF = \frac{\text{Viscosity of a solution with 57.6 mg Ca}^{2+}/\text{g pectin}}{\text{Viscosity of a solution with 0.0 mg Ca}^{2+}/\text{g pectin}}$$

Pectic enzymes are classified according to their mode of attack on the galacturonan part of the pectin molecule. In particular, pectin methylesterases, otherwise referred to as PMEs, de-esterify HE pectins to LE pectins or pectic acids. In contrast, and by way of example, pectin depolymerases split the glycosidic linkages between galacturonosyl methylester residues.

In more detail, PME activity produces free carboxyl groups and free methanol. The increase in free carboxyl groups can be easily monitored by automatic titration. In this regard, earlier studies have shown that some PMEs de-esterify pectins in a random manner, in the sense that they de-esterify any of the esterified (e.g. methylated) galacturonic acid residues on one or more than one of the pectin chains. Examples of PMEs that randomly de-esterify pectins may be obtained from fungal sources such as Aspergillus aculeatus (see WO 94/25575) and Aspergillus japonicus (Ishii et al 1980 J Food Sci 44 pp 611–14). Baron et al (1980 Lebensm. Wiss. M-Technol 13 pp 330–333) apparently have isolated a fungal PME from Aspergillus niger.

PMEs have also been reported by Versteeg et al (J Food Sci 45 (1980) pp 969–971), and in WO-A-97/03574 and in WO-A-97/31102.

In contrast to de-esterifying pectins in a random manner, some PMEs are known to de-esterify pectins in a block-wise manner, in the sense that it is believed they attack pectins either at non-reducing ends or next to free carboxyl groups and then proceed along the pectin molecules by a single-chain mechanism, thereby creating blocks of un-esterified galacturonic acid units which can be calcium sensitive. Examples of such enzymes that block-wise enzymatically de-esterify pectin are plant PMEs. Up to 12 isoforms of PME have been suggested to exist in citrus. These isoforms have different properties.

Random or blockwise distribution of free carboxyl groups can be distinguished by high performance ion exchange chromatography. These tests are often used to check for undesirable, residual PME activity in citrus juices after pasteurization because residual PME can cause, what is called, "cloud loss" in orange juice in addition to a build up of methanol in the juice.

PME substrates, such as pectins obtained from natural plant sources, are generally in the form of a high ester pectin having a DE of about 70%. Sugar must be added to extracts containing these high ester PME substrates to provide sufficient soluble solids to induce gelling. Usually a minimum of 55% soluble solids is required. Syneresis tends to occur more frequently when the percentage soluble solids is less than 55%. When syneresis does occur, expensive additives must be used to induce gelling.

As reported in PCT/IB98/00673 (filed Apr. 24, 1998), a benefit derived from use of a PME in the preparation of, for example, a foodstuff will depend to some extent on the quality and quantity and type of the PME used and on the quality and quantity and type of the PME substrates—in particular pectin—that may be present in the material used to prepare the foodstuff. For example, if the substrate is a fruit material or a vegetable material then the amount and/or structure of natural pectin in that substrate will be different for different types of fruit material or vegetable material. This is also borne out by the data presented in WO-A-94/25575, especially FIG. 7 where it is clear to see that its PME system is not ideal.

Thus, the structure of a pectin—either pre- or post-treatment such as treatment with enzyme(s) and/or chemical (s)—will determine the resultant properties of the pectin.

Hence, it is desirable to have some knowledge about the structure of a pectin before it is used in, for example, a process for preparing a foodstuff.

In trying to determine some structural knowledge about pectins, workers are often dependent on the type and quality of the pooled material and, in addition, the type of destructive extraction methods that are used. This can lead to an incomplete or misleading picture of pectin structure in the context of cell wall architecture and cell development.

In order to avoid these problems, immunolocalization studies using monoclonal antibodies (mAbs) have been proposed. In this regard, it has been suggested that these mAbs could be used to try to ascertain the distribution of pectin at the cellular level—which is a crucial aspect of understanding pectin function.

However, to date, the mAb probes that are currently available have a limited usefulness. For example, they are not specific and they are only effective in the study of a fraction of the pectic structural elements so far characterized.

Thus, it is desirable to provide a means of detecting certain desirable motifs on a pectin (including a component thereof or a composition comprising either).

SUMMARY OF THE INVENTION

In one aspect, the present invention provides an antibody having one or more of the following features: (a) it is capable of binding to a de-esterified homogalacturonan; and (b) it comprises the amino acid sequence presented as SEQ ID No. 1 or a variant, homologue, derivative or fragment thereof.

The antibody of the present invention does not bind to other pectin structures—such as polymannuronic acid and polyguluronic acid, as well as arabinans.

According to further aspects of the present invention there is provided:

An antibody comprising the amino acid sequence presented as SEQ ID No. 1 or a variant, homologue, derivative or fragment thereof.

An antibody having the amino acid sequence presented as SEQ ID No. 1.

The term "antibody", as used herein with reference to the present invention, refers to a complete antibody or an antibody fragment or an antibody component, as well as any combination thereof, capable of binding to the selected target—namely the pectin structure identified herein above.

Antibody fragments and components include Fv, ScFv, dsFv, Fab, F(ab), Fab', F(ab)2, F(ab')2, Facb, monoclonal and polyclonal antibodies, engineered antibodies including chimeric, CDR-grafted antibodies, and artificially selected antibodies produced using phage display or alternative techniques. Small fragments, such Fv and ScFv, possess advantageous properties for analytical applications.

Preferably the antibody is linked to a detectable moiety.

Any suitable detectable moiety can used. The moiety can be directly detectable —such as a radiolabelled moiety, a moiety comprising a dye that is capable of producing a visually detectable signal (which need not necessarily be detectable by means of the naked eye) or a luminescent moiety. The moiety can be indirectly detectable—such as an enzyme moiety that is capable of acting on a substrate that is itself capable of generating a detectable signal or a moiety that is itself recognized by a labelled antibody.

The term "linked" includes direct attachment—such as through a direct bond, e.g. an ionic bond or a covalent bond.

Other aspects of the present invention include:

A process comprising linking the antibody according to the present invention with a detectable moiety.

Use of an antibody according to the present invention to identify a pectin motif.

Other aspects of the present invention include:

A nucleotide sequence coding for the antibody according to the present invention.

A nucleotide sequence comprising the sequence presented as SEQ ID No. 2 or a variant, homologue, derivative or fragment thereof A nucleotide sequence having the sequence presented as SEQ ID No. 2 or a variant, homologue, derivative or fragment thereof A nucleotide sequence having the sequence presented as SEQ ID No. 2.

A process for preparing an antibody comprising expressing the nucleotide sequence according to the present invention.

Preferably the nucleotide sequence is within a host cell, such as a transformed cell.

Thus, the present invention also encompasses:

A host cell (such as a transformed cell) comprising the nucleotide sequence according to the present invention.

A host cell (such as a transformed cell) capable of secreting the antibody according to the present invention.

A host cell (such as a transformed cell) secreting the antibody according to the present invention.

Preferably the nucleotide sequence is DNA.

For some aspects, preferably the nucleotide sequence is cDNA.

Other aspects of the present invention include:

An assay comprising:
a) contacting a pectin with an antibody according to the present invention;
b) determining whether the antibody associates with the pectin.

The term "associates" includes binding, which need not necessarily be irreversible binding.

An assay comprising:
a) providing a pectin composition;
b) removing at least a portion of that pectin composition;
c) contacting at least a part of the portion of that pectin composition with an antibody according to the present invention;
d) determining whether the antibody associates with the pectin within that part.

A method comprising:
a) providing a pectin composition;
b) removing at least a portion of that pectin composition;
c) contacting at least a part of the portion of that pectin composition with an antibody according to the present invention;
d) determining whether the antibody associates with the pectin within that part;
e) admixing the remainder of the pectin composition with one or more food ingredients.

A process comprising
a) providing a pectin;
b) treating the pectin;
c) contacting at least a portion of the treated pectin with an antibody according to the present invention;
d) determining whether the antibody associates with the treated pectin; and optionally
e) using the treated pectin to prepare a food.

A food prepared by the method or process of the present invention These aspects and other aspects of the present invention are now discussed in more detail.

DETAILED DESCRIPTION OF THE PREFERRED EMBODIMENTS

The present invention provides antibodies useful for the detection of a pectin motif. The antibodies of the present invention are sometimes referred to as PAM1 and PAM2. The antibodies according to the invention may be linked to a label. The antibodies may be used as an assay to see if a particular pectin composition has the pectin motif or can be used to prepare a food. The food may be for animal and/or human consumption. Preferably, the food is for human consumption. The term "pectin" as used in relation to the present invention includes pectin per se, fractions thereof and components thereof, including compositions comprising same or compositions thereof.

The pectin comprises at least a HG region.

Preferably, the pectin comprises one or more de-esterified regions. Preferably, the pectin comprises one or more block-wise de-esterified regions.

For some applications, preferably the block-wise de-esterified pectin is sensitive to $Ca^{2+}$ ions.

For some applications, preferably the block-wise de-esterified pectin is insensitive to $Ca^{2+}$ ions.

More preferably, the pectin comprises a region of at least about 20—preferably at least about 25, more preferably at least about 30—contiguous de-esterified residues of GalA.

The pectin may be treated with enzymes and/or chemicals.

Preferably, the pectin has been pre-treated with at least one enzyme. In one preferred aspect, that enzyme is an enzyme prepared by use of recombinant DNA techniques.

Preferably, the pectin has been pre-treated with a PME. Preferably, the PME has the ability to de-esterify pectin in a block-wise manner. A preferred PME is a plant PME.

The present invention is advantageous for a number of reasons.

By way of example, it provides a means of detecting certain desirable motifs on a pectin. Also, it provides a means to allow for the assessement of the suitablity of a particular pectin for a specific purpose. Also, it provides a means to allow for the assessement of the suitablity of a particular pectin for food applications—such as in the preparation of jams, gels, yogurts—including drinking yogurts. The antibody may even be used as a means to extract suitable pectins—e.g. the antibody may be bound to, for example, the inner wall of a column through which can be passed a pectin composition containing different pectins, here at least a portion of the desirable pectin fractions will be separated from the remainder of the pectin composition. In addition, the nucleotide sequence of the present invention can be used to transform plants, such that the transformed plants will affect pectin composition in planta. In addition, the antibody could be used to quantify the amount of pectin in a sample, which pectin having the motif as described herein. In addition, the antibody could be used to in a process to extract pectin from a sample, which pectin having the motif as described herein, by binding the pectin to the antibody—which itself may be bound to a solid support. The extracted pectin could then be used to prepare, for example, a foodstuff—such as a yogurt, more in particular a drinking yogurt.

In the general sense the present invention relates to an antibody comprising the amino acid sequence presented as SEQ ID No. 1 or a variant, homologue, derivative or fragment thereof.

The terms "variant", "homologue", "derivative" or "fragment" in relation to the amino acid sequence of the present invention include any substitution of, variation of, modification of, replacement of, deletion of or addition of one (or more) amino acid from or to the sequence providing the resultant amino acid sequence has the ability to bind to pectin, preferably having at least the same binding activity of the amino acid shown as SEQ I.D. No. 1. In particular, the term "homologue" covers identity with respect to structure and/or function providing the resultant amino acid sequence has binding activity. With respect to sequence identity (i.e. similarity), preferably there is at least 75%, more preferably at least 85%, more preferably at least 90% sequence identity. More preferably there is at least 95%, more preferably at least 98%, sequence identity. Preferably sequence identity relates to at least the CDR region. The above terms also encompass allelic variations of the sequences.

In addition, in another general sense the present invention relates to a nucleotide sequence comprising the sequence presented as SEQ ID No. 2 or a variant, homologue, derivative or fragment thereof.

The terms "variant", "homologue", "derivative" or "fragment" in relation to the nucleotide sequence of the present invention include any substitution of, variation of, modification of, replacement of, deletion of or addition of one (or more) nucleic acid from or to the sequence providing the resultant expression product thereof has binding activity, preferably having at least the same binding activity of the amino acid sequence shown as SEQ I.D. No. 1. In particular, the term "homologue" covers identity with respect to structure and/or function providing the resultant expression product thereof has binding activity. With respect to sequence identity (i.e. similarity), preferably there is at least 75%, more preferably at least 85%, more preferably at least 90% sequence identity. More preferably there is at least 95%, more preferably at least 98%, sequence identity. Preferably sequence identity relates to at least the CDR region. The above terms also encompass allelic variations of the sequences.

Sequence identity for both the amino acid sequences and the nucleotide sequences can be determined by a simple "eyeball" comparison (i.e. a strict comparison) of any one or more of the sequences with another sequence to see if that other sequence has, for example, at least 75% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Advantageously, the BLAST algorithm is employed, with parameters set to default values. The BLAST algorithm is described in detail at Internet website:www.ncbi.nih.gov/BLAST/blast_help.html, which is incorporated herein by reference. The search parameters are defined as follows, can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see Internet website:www.ncbi.nih.gov/BLAST/blast_help.html) with a few enhancements. The BLAST programs were tailored for sequence similarity searching, for example to identify homologues to a query sequence. For a discussion of basic issues in similarity searching of sequence databases, see Altschul et al (1994) Nature Genetics 6:119–129.

The five BLAST programs available at Internet website:www.ncbi.nlm.nih.gov perform the following tasks:

blastp—compares an amino acid query sequence against a protein sequence database.

blastn—compares a nucleotide query sequence against a nucleotide sequence database.

blastx—compares the six-frame conceptual translation products of a nucleotide query sequence (both strands) against a protein sequence database.

tblastn—compares a protein query sequence against a nucleotide sequence database dynamically translated in all six reading frames (both strands).

tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman (see Internet websit:www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN" and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect.

Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at Internet website:www.ncbi.nlm.nih.gov/BLAST.

Other computer program methods to determine identify and similarity between the two sequences include but are not limited to the GCG program package (Devereux et al 1984 *Nucleic Acids Research* 12: 387) and FASTA (Atschul et. al 1990 *J Molec. Biol.* 403–410).

In some aspects of the present invention, no gap penalties are used when determining sequence identity.

The present invention also encompasses nucleotide sequences that are complementary to the sequences presented herein, or any fragment or derivative thereof. If the sequence is complementary to a fragment thereof then that sequence can be used as a probe to identify similar sequences.

The present invention also encompasses nucleotide sequences that are capable of hybridizing to the sequences presented herein, or any fragment or derivative thereof.

Hybridization means a "process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach CW and GS Dveksler (1995, PCR Primer, a Laboratory Manual, Cold Spring Harbor Press, Plainview N.Y.).

Also included within the scope of the present invention are nucleotide sequences that are capable of hybridizing to the nucleotide sequences presented herein under conditions of intermediate to maximal stringency. Hybridization conditions are based on the melting temperature (Tm) of the nucleic acid binding complex, and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related nucleotide sequences.

In a preferred aspect, the present invention covers nucleotide sequences that can hybridize to the nucleotide sequence of the present invention under stringent conditions (e.g. 65° C. and 0.1×SSC).

The present invention also encompasses nucleotide sequences that are capable of hybridizing to the sequences that are complementary to the sequences presented herein, or any fragment or derivative thereof. Likewise, the present invention encompasses nucleotide sequences that are complementary to sequences that are capable of hybridizing to the sequence of the present invention. These types of nucleotide sequences are examples of variant nucleotide sequences. In this respect, the term "variant" encompasses sequences that are complementary to sequences that are capable of hydridizing to the nucleotide sequences presented herein. Preferably, however, the term "variant" encompasses sequences that are complementary to sequences that are capable of hydridizing under stringent conditions (eg. 65° C. 0.1×SSC {1×SSC 0.15 M NaCl, 0.015 Na$^3$ citrate pH 7.0}) to the nucleotide sequences presented herein.

The antibody of the present invention was identified using phage-display technology. This is in contrast to the earlier work that has been carried out on mAbs for pectins. Here, most of the anti-pectin mAbs produced to date have been generated using hybridoma technology. However, antibody phage display technology offers an extremely powerful approach for exploiting the immense diversity of the mammalian immune system, while by-passing immunization and allowing the in vitro manipulation of the affinity and specificity of the antibody binding fragments. Moreover, antibodies may be produced that have specificities not readily produced by hybridoma technology. Antibody phage libraries are constructed by the fusion of rearranged antibody variable region genes (V-genes) to genes encoding phage coat proteins, for example the M13 coat protein gene III. Expression of the fusion product results in the antibody fragment being presented on the phage surface, and since each phage particle also carries the genetic material encoding the displayed antibody fragment, the nucleotide sequence encoding selected antibody fragments may be readily determined and manipulated. Antibodies are selected by panning phage libraries against immobilized antigen. Only phage expressing appropriate antibody fragments are retained and subsequently re-amplified, while non-binding phage are removed by washing.

One approach for selecting phage antibodies is to construct a library for each antigen of interest using antibody gene sequences derived from lymphocytes of immunized animals. This has been achieved for the preparation of a phage antibody against RGII. Alternatively, a single, extremely large naive combinatorial library may be constructed from antibody V-genes derived from an un-inmunized donor and used to screen for phage antibodies against all antigens. This 'single pot' approach has the significant advantages that animal immunization is completely by-passed, the time consuming process of library construction is avoided by all but the first user and antibodies may be produced against non-immunogenic substances.

In accordance with the present invention, here we report the selection from a naive phage antibody library of monoclonal antibodies specific to de-esterified HG blocks.

As indicated above, the present invention also encompasses a process for preparing an antibody comprising expressing the nucleotide sequence according to the present invention. In one preferred aspect, the nucleotide sequence may be present in a host cell (such as a transformed cell).

Generally applicable teachings to antibodies—as well as to the large scale production thereof—now follow.

Antibodies according to the invention may be produced in any suitable cell culture. This may be accomplished via bacterial, yeast, fungal, plant or more preferably via mammalian cell culture. The selected cell culture system preferably secretes the antibody product.

Therefore, the present application includes a process for the production of an antibody or antibody fragment according to the invention. This method comprises culturing a host, e.g. E.coli, yeast or a mammalian cell line, under conditions that allow for expression of the nucleotide sequence of the present invention. Preferably, the host cell is a transformed cell. Typically the host cell is prepared by transforming a cell with a cassette comprising at least the nucleotide sequence of the present invention in order to form the transformed cell. A typical vector for the transformation is a hybrid vector harboring an expression cassette. This expression cassette may comprise a promoter operably linked to a first DNA sequence encoding a signal peptide linked in the proper reading frame to a second DNA sequence encoding the antibody or antibody fragment, and isolating said antibody or antibody fragment.

Multiplication of hybridoma cells or mammalian host cells in vitro is carried out in suitable culture media known to those skilled in the art, for example Dulbecco's Modified Eagle Medium (DMEM) or RPMI 1640 medium, optionally supplemented with a mammalian serum, e.g. foetal calf serum, or with trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in Luria Broth (LB), NZCYM, NZYM, NZM, Terrific Broth, SOB, SOC, 2 x YT, or M9 Minimal Medium, and for yeast in YPD, YEPD, Minimal Medium, or Complete Minimal Dropout Medium.

The cell culture supernatants are screened for the presence of the desired antibodies, preferably by immunofluorescent staining, by immunoblotting, by an enzyme immunoassay, e.g. a sandwich assay or a dot-blot assay, by a radioimmunoassay, or by any other suitable technique known to those skilled in the art.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, for example mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

For isolation of the antibodies, the immunoglobulins in the culture supernatants or in the ascitic fluid may be concentrated, for example by precipitation with ammonium sulphate, by dialysis against hygroscopic material such as polyethylene glycol, by filtration through selective membranes, or the like. Optionally, the antibodies may be purified by chromatography, for example gel filtration, ion-exchange chromatography, chromatography over DEAE-cellulose, or affinity chromatography. Affinity chromatography may be with the target of interest (namely the pectin structure as defined herein-above), or with a super-antigen such as Protein-A, Protein-G, Protein-L and the like.

The present invention further concerns hybridoma cells secreting monoclonal antibodies of the invention. The preferred hybridoma cells of the invention are genetically stable, secrete monoclonal antibodies of the invention of the desired specificity and can be recovered from cryogenically preserved cultures by thawing and sub-culturing.

The invention also concerns a process for the preparation of a hybridoma cell line secreting monoclonal antibodies directed against the target of this invention. Such a method is characterized in that a suitable mammal, for example a Balb/c mouse, is immunized with purified target, or with a carrier bearing a purified target, or with cells bearing the target. After an appropriate schedule of immunization, known to those skilled in the art, antibody-producing cells of the immunized mammal are fused with cells of a suitable myeloma cell line, the hybrid cells obtained in the fusion are cloned, and cell clones secreting the desired antibodies are selected. For example, spleen cells of Balb/c mice immunized with cells bearing the target of interest are fused with cells of the myeloma cell line PAI or the myeloma cell line Sp2/0-Ag14. The resulting hybrid cells are screened for secretion of the desired antibodies, and those found to be expressing such antibodies are cloned.

The invention also concerns recombinant nucleic acids comprising an insert coding for a heavy chain variable domain and/or for a light chain variable domain of antibodies directed to the target molecule as described above. By definition, such nucleic acids include single stranded coding DNAs, double stranded DNAs consisting of a coding DNA strand and of a complementary DNA strand, or these complementary (single stranded) DNAs themselves.

Furthermore, DNA encoding a heavy chain variable domain and/or a light chain variable domain of antibodies directed to the target molecule of the invention, can be enzymatically or chemically synthesized DNA having the authentic DNA sequence coding for a heavy chain variable domain and/or for a light chain variable domain, or a variant thereof. A variant of the authentic DNA is a DNA encoding a heavy chain variable domain and/or a light chain variable domain of the above-mentioned antibodies in which one or more amino acids are added, deleted or exchanged with one or more other amino acids. Preferably said modification(s) are outside the CDRs of the heavy chain variable domain and/or of the light chain variable domain of the antibody. Such a DNA variant may also include 'silent' mutations where one or more nucleotides are replaced by other nucleotides, and where the DNA variant thus created codes for an unchanged sequence of amino acid(s). Such a variant nucleotide sequence may also be a degenerate nucleotide sequence. Such nucleotide sequences are degenerate with reference to the genetic code in that an unlimited number of nucleotides are replaced by other nucleotides without resulting in a change of the amino acid sequence originally encoded. Such degenerate sequences may be useful due to their different restriction sites and/or frequency of particular codons which may be preferred by a specific host, for example *E. coli*, to obtain optimal expression of a heavy chain variable domain and/or a light chain variable domain. Such DNA variants are easily obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention also encompasses recombinant DNAs comprising an insert coding for a heavy chain variable domain of an antibody directed against the target molecule, fused to a constant domain γ for example γ1, γ2, γ3 or γ4, preferably Δ1 or γ4. Likewise the invention concerns recombinant DNA,s comprising an insert coding for a light chain variable domain, of an antibody directed against the target of interest, fused to a constant domain κ or λ, preferably κ.

In another embodiment the invention relates to recombinant DNAs coding for a polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a protease cleavage site and/or a peptide spacer and/or an effector molecule.

Antibodies and antibody fragments according to the invention are useful in analysis of pectins. Accordingly, the invention provides a composition for the analysis of pectin comprising an antibody according to the invention.

In the case of an analytical composition, the antibody is preferably provided together with means for detecting the antibody, which may be enzymatic, fluorescent, radioisotopic or other suitable means. The antibody and the detection means may be provided for simultaneous, simultaneous separate or sequential use, in a kit intended for use in analysis.

In summary, the present invention provides an antibody useful for the detection of a pectin motif. The antibody of the present invention is sometimes referred to as PAM1. As indicated above, the antibodies according to the invention may be linked to a label. Especially preferred are labels which allow the imaging of the distribution of the antibody in vivo. Such labels may be radioactive labels or radioopaque labels, such as metal particles, which are readily visualized. Moreover, they may be fluorescent labels or other labels which are detectable in tissue samples. Recombinant DNA technology may be used to improve the antibodies of the invention.

As shown in the Examples Section, the present invention also provides a further antibody which is useful for the detection of a pectin motif. This other antibody of the present invention is sometimes referred to as PAM2. The sequence for PAM2 is shown as SEQ ID No. 3. Thus, the above teachings relating to PAM1 are also applicable to PAM2. At present, and due to the slightly different binding characteristics of PAM2, it is envisioned that for some applications it is preferable to use PAM1 rather than PAM2. Nevertheless, PAM2 is still a useful entity.

BRIEF DESCRIPTION OF THE DRAWINGS

The present invention will now be described only by way of examples in which reference is made to the following Figures.

(A) The binding of PAM1 to a range of OGAs with a range of DPs (degrees of polymerization) was assessed by competitive inhibition ELISA with PGA as the immobilized antigen. PAM1 bound weakly to a sample containing an mixture of OGAs with DPs from 13–16 and strongly to PGA.

(B) OGAs with defined DPs were produced by the fractionation of autoclaved PGA by HPAEC-PAD (top trace). The DP of fractions was determined by reference to the retention time of an OGA with a DP of 7 (bottom trace). Selected fractions with the DP ranges indicated were applied to nitrocellulose and probed with PAM1.

Figure 3:
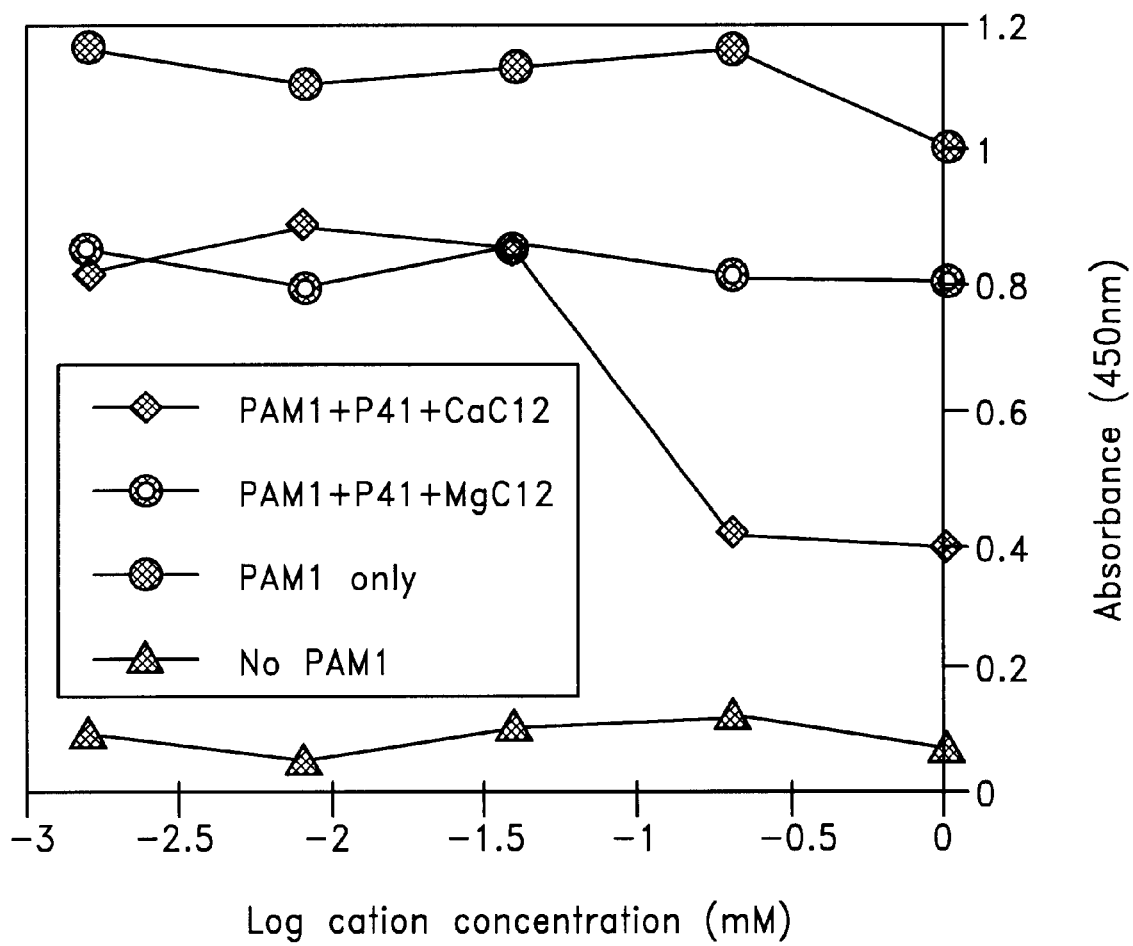

FIG. 3. The effect of divalent cations on PAM1 binding. The binding of PAM1 in the presence of added calcium chloride or magnesium chloride in competitive inhibition ELISA with PGA as the immobilized antigen and P41 as the competitor.

FIG. 4. The molecular anatomy of the PAM1 and PAM2 scFvs.

(A) Schematic representation of the genes encoding PAM1 and PAM2 scFvs showing the spatial organization of the functional components and primers used for sequencing. The diagram is drawn approximately to scale with respect to length, except for the primers, for which the tips of arrowheads indicate 5' ends. The ribosome binding site (RBS), the pelB leader sequences (pelB), complementarity determining regions (CDR) 1, 2, and 3, the sequence joining the variable heavy (VH) chain and variable light (VL) chains (linker), the myc epitope tag (myc) and the M13 coat protein gene coding region (gIII) are shown.

(B) Amino acid sequence alignments of the PAM1 (SEQ ID NO:1) and PAM2 (SEQ ID NO:3) scFvs. Both scFvs consist of light chain (single underlined) and heavy fragments joined by a linker sequence (boxed in dark grey). Non-identical heavy chain sequence is boxed in black and CDRs 1, 2 and 3 are underscored with +, * and ~ respectively. The pelB leader sequence (boxed in light grey) precedes the heavy chain fragment. The myc epitope at the carboxyl end of the light chain fragment is double underlined. The light chain is joined to the pIII coat protein via a stretch of sequence (italicized) containing and amber stop codon encoding glutamic acid (E).

DETAILED DESCRIPTION OF THE INVENTION

The present invention relates to antibodies. In particular, the present invention relates to antibodies that are capable of recognizing a certain motif on a pectin structure. These antibodies are designated PAM1 and PAM2. The following examples will provide materials and methods to produce the antibodies of the present invention. Although other materials and methods similar or equivalent to those described herein can be used in the practice or testing of the present invention, the preferred methods and materials are now described. Example 1 describes the steps required to prepare the polysaccharides and oligosaccharides used in the following assays.

EXAMPLE 1

Pectic polysaccharides and oligosaccharides

Polysaccharides and OGAs used in immunoassays were obtained as follows: Pectins with a range of DEs produced by digestion of a high ester lime pectin with plant or fungal PME; oligogalacturonides of defined DPs and OGA mixtures; RGI and RG II; defined HG of blocksize (70 (97% GalA), acetylated-HG (with a degree of acetylation of 49%) and xylogalacturonan; and polymannuronic and polyguluronic acids.

EXAMPLE 2

Selection of anti-pectin binding phagemids

Phagemids with anti-pectin properties were selected from the Synthetic scFv Library (#1) (Nissim et al., 1994 EMBO J. 13, 692–697) which was provided by the Centre for Protein Engineering, MRC Centre, Cambridge, UK. The library was panned for pectin binding phage using immunotubes (Maxisorb, Nunc, Denmark). For each round of panning, an immunotube was coated overnight at 4° C. with 4 ml of a 100 mg/ml solution of pectin with a degree of esterification of 23%, (LE23) in phosphate-buffered saline (PBS). After coating, immunotubes were washed three times in PBS and blocked with 4 ml of 2% fat free milk powder (Marvel) in PBS (2% MPBS) for 2 hr at room temperature. Phage were added to immunotubes in 2% MPBS and incubated for 30 min with continuous rotation and for 90 min stationary, all at room temperature. Non-binding phage were removed by 20 washes with PBS with 0.1% (v/v) Tween 20 followed by 20 washes with PBS. Bound phage were eluted with 1 ml of 100 mM triethylamine and infected into E. coli (strain TG1), from which glycerol stocks were produced after overnight growth. To amplify phage populations, infected E. coli were infected with helper phage (VCS M13, Stratagene) and after overnight growth excized phagemids were harvested by polyethylene glycol/sodium chloride precipitation (to produce a titre of at least 1013 phage/ml) and used in subsequent panning rounds. A control phage monoclonal antibody with specificity directed against maltose binding protein was provided by the Centre for Protein Engineering, MRC Centre, Cambridge, U.K.

EXAMPLE 3

Selection of monoclonal phage antibodies

After four panning rounds, 192 colonies from the final polyclonal population were individually grown and screened for pectin binding activity by direct antibody capture ELISA. Microtitre plates (Maxisorb, Nunc, Denmark) were coated overnight at 4° C. with LE23 at 50 (g/ml in PBS. After three PBS washes plates were blocked with 2% MPBS for 2 hr at room temperature then washed again three times with PBS. 20 ml of amplified and precipitated monoclonal phage populations were added to wells with 80 ml 2% MPBS (to give a final phage concentration of approximately $2 \times 10^{12}$ phage/ml) and incubated for 90 min. Non-binding phage were removed with three washes of PBS containing 0.05% Tween 20 followed by three washes with PBS. To detect bound phage, 100 ml of anti-M13 antibody conjugated to horse radish peroxidase anti-M13/HRP, Pharmacia) was added to wells, diluted 1/1000 in 2% MPBS to and incubated for 90 min at room temperature. After three washes of PBS containing 0.05% Tween 20 followed by three washes with PBS, plates were developed with 150 (μl per well of a tetramethyl benzidine-based substrate. After stopping the reaction with 35 ml/well 2 M sulphuric acid, absorbances were read at 450 nm.

EXAMPLE 4

Immunoblot selection and characterization of monoclonal phage antibodies

Test solutions of pectins and control polysaccharides were dissolved in deionized water or Tris-buffered saline (TBS) and spotted directly onto nitrocellulose in 1 ml aliquots, usually serially from 10 mg/ml stock solutions. After drying for approximately 30 min blots were blocked with 5% MPBS then incubated with approximately $10^{12}$ phage/ml in 5% MPBS for 2 hr. After extensive washing in tap water blots were incubated for 2 hr in anti-M13/HRP diluted 1/1000 in 5% MPBS. After further washing with tap water, blots were developed by incubation in chloro-naphthol-based substrate solution. All incubations were at room temperature.

EXAMPLE 5

Competitive Inhibition ELISAs

Competitive inhibition ELISAs were used to assess binding in solution of phage antibody to potential oligosaccharide and polysaccharide inhibitors. Microtitre plates (Maxisorb, Nunc, Denmark) were coated overnight at 4ø C. with 50 (g/ml polygalacturonic acid (PGA) in TBS (100 ml/well). After brief washing in tap water plates were blocked with 3% ELISA-grade bovine serum albumin (3% BSA) for 2 hr at room temperature (200 ml/well). Following brief washing with tap water, competitor solutions were applied (100 ml/well) as serial dilutions in 3% BSA then phage monoclonal antibodies at a level of approximately $10^{10}$ phage/ml. After 2 hr incubation plates were washed extensively with tap water and anti-M13/HRP secondary antibody applied (100 ml/well) diluted 1/7500 in 3% BSA and incubated for 2 hr at room temperature. Following extensive washing in tap water plates were developed as described previously. Concentrations of competitors resulting in 50% inhibition (IC50) of antibody binding were determined by plotting competitor concentrations against absorbance. Values from controls with no competitor were taken as 0% inhibition of antibody binding, and values from controls with no antibody represented 100% inhibition of binding. In order to assess the effect on antibody binding of divalent cations, ELISAs were performed as described above except that pectin solutions were added at a concentration of 10 mg/ml to all wells, while cations or the calcium chelator (trans-1,2-diaminocyclohexane-N,N,N',N'-tetraacetic acid, CDTA) were serially diluted.

EXAMPLE 6

Imunofluorescent localization of oligogalacturonide epitopes

Plant tissue was fixed in 4% paraformaldehyde in 50 mM PIPES (1,4-piperazine-diethanesulphonic acid), 5 mM $MgSO_4$, and 5 mM EGTA (ethylene glycol bis ((-aminoethyether)-N,N,N',N'-tetraacetic acid) pH 6.9 overnight at 4° C., dehydrated in a graded ethanol series and embedded in LR white acrylic resin (London Resin Co., UK). Sections (0.5–1 m thick) were applied to multiwell slides coated with Vector bond (Vector laboratories, UK) and blocked with 5% MPBS for 30 min then washed with PBS. Phage antibodies were applied for 1 hr at a level of approximately $10^{12}$ phage/ml, diluted in 5% MPBS. After washing with PBS, anti-M13 antibody (Pharmacia) was applied for 1 hr as a 1/50 dilution in 5% MPBS. Following washing with PBS, anti-mouse antibody conjugated to fluorescein isothiocyanate (anti-mouse/FITC, Sigmna) was applied for 1hr as a 1/100 dilution in 5% MPBS. Finally, sections were washed with PBS, mounted in PBS/glycerol based antifade solution (Citifluor), examined with a microscope equipped with epifluorescence and micrographs were taken on 400ASA color slide film (Kodak).

EXAMPLE 7

HPAEC-PAD

OGAs with DPs over 20were analysed using a Dionex high-performance anion-exchange chromatography system with pulsed amperometric detection (HPAEC-PAD). Autoclaved PGA (2.5 mg) was applied to a PA100 column and gradient eluted with 0.8 ml/min potassium oxalate (pH 6.0) with the post-column addition of 0.2 ml/min of 500 mM potassium hydroxide. The stepped gradient of potassium oxalate had the following profile: 25 mM, increasing to 100 mM (from 1 to 9 min), to 200 mM (from 9 to 40 min), to 250 mM (from 40 to 65 min), to 265 mM (from 65 to 80 min) and 500 mM (from 80 to 100 min). 1 ml fractions were collected, immediately neutralized with the addition of Tris buffer (1 M, pH 7.2) and applied in 50 ml aliquots to nitrocellulose sheets using a vacuum manifold device (Stratagene, USA). Nitrocellulose sheets were subsequently probed with PAM1 as described previously for immuno-dot-blots.

EXAMPLE 8

Sequencing of phage antibody clones

Plasmid DNA from selected phagemid clones was isolated using a plasmid purification kit (Qiagen, USA). Genes encoding scFvs were sequenced using the oligonucleotide primers:

```
LMB3
(5'-CAGGAAACAGCTATGAC-3')        SEQ ID #5 fd-SEQ1
(5'-GAATTTTCTGTATGAGG-3')        SEQ ID #6 and PAM seq1
(5'-TGAGGCTGTCTCCTTGG-3').       SEQ ID #7
```

Nucleotide sequences were obtained by the Sanger dideoxy method using an automated DNA sequencer (Applied Biosystems). Sequences were aligned to their closest germline counterparts using V BASE (Internet website:www.mrc-cpe.cam.ac.uk/imt-doc/restricted/ok.html) using the DNAPLOT alignment package (Internet website www.mrc-cpe.cam.ac.uk/imt-doc/restricted/DNAPLOT.html).

EXAMPLE 9

SPECIFIC DETERMINATION TECHNIQUES

MALDI-TOF-MS

Galacturonic acid oligomers of defined length were prepared by acid hydrolyses of URS pectin. The oligomers were separated by gelfiltration and characterized by matrix assisted laser desorption ionization time-of-flight mass spectrometry (MALDI-TOF-MS). The mass determination revealed that fragments composed of three to about 40 galacturonic acids elute together. The different fragments may be separated by Dionex in order to obtain samples of galacturonic acid oligomers of well defined structure.

By MALDI-TOF-MS it has been determined that it is possible to analyse fragments composed of three to 8 galacturonic acids without sodium or potassium ions. Fragments composed of eight to 14 galacturonic acids attach one sodium ion and fragments of fifteen to 30 galacturonic acids at least two sodium ions. The attachment of sodium ions largely decreases the quality of the spectra. It may be possible to replace the sodium ions with ammonium ions as they do not interfere with mass determination.

ESI-MS

Electrospray Ionization (ESI)/Ion Trap Mass Spectrometry was used to measure small galacturonic acid oligomers (up to 10-mers). Electrospray Ionization is very sensitive towards contaminations in the sample. The oligogogalacturonic acids were purified and separated using anion exchange chromatography and the first spectra were of poor quality due to extensive sodium adduct formation. Spectra were acquired in positive and negative ionization mode. The spectra recorded in negative mode showed higher ion abundances and better signal to noise ratios. In order to purify the samples, small columns loaded with ca. 2 μl cation exchange beads (BioRad, AG 50W-X8 Resin) were used for desalting. Sodium ions are exchanged with ammonnium ions by passing the solution over the column. Ammonium ions do not deterioate the spectrum quality because of their volatile character. Small galacturonic acid oligomers were fragmented in the ion trap mass spectrometer. As expected, the main fragmentation pathway is the loss of a complete galacturonic acid unit.

EXAMPLE 10

Selection of anti-homogalacturonan phage antibodies

Anti-homogalacturonan specific antibodies were selected from a naive phage display library known as the Synthetic scFv Library (#1) (Nissim et al., 1994 EMBO J. 13, 692–697) which was provided by the Centre for Protein Engineering, MRC Centre, Cambridge, UK. An anti-pectin polyclonal phage population was produced after four rounds of immunopanning against a low ester pectin (LE23) with a degree of esterification (DE) of 23%, during which the titre of recovered phage increased approximately 1800-fold. Monoclonal phage antibodies were produced by selecting 192 colonies from the polyclonal population and screening against LE23 by ELISAs. Approximately 40% of the selected clones showed strong reactivity against LE23. Clones with binding specificity directed against de-esterified HG were selected from this group by further differential ELISA screening against polygalacturonic acid (PGA) and high ester pectin (HE81) with a DE of 81%. Two clones (designated PAM1 and PAM2) were selected that showed strong reactivity against PGA but very weak reactivity against HE81. PAM1 and PAM2 showed identical specificity in all subsequent assays but differed in that PAM1 had a higher avidity. In antibody capture ELISAs (with PGA as the immobilized antigen), the antibody concentration required to achieve 30% maximal binding of PAM1 was approximately 250-fold lower for PAM1 compared with PAM2. Antibody concentrations from $10^8$–$10^{13}$ were tested.

Figure 1:
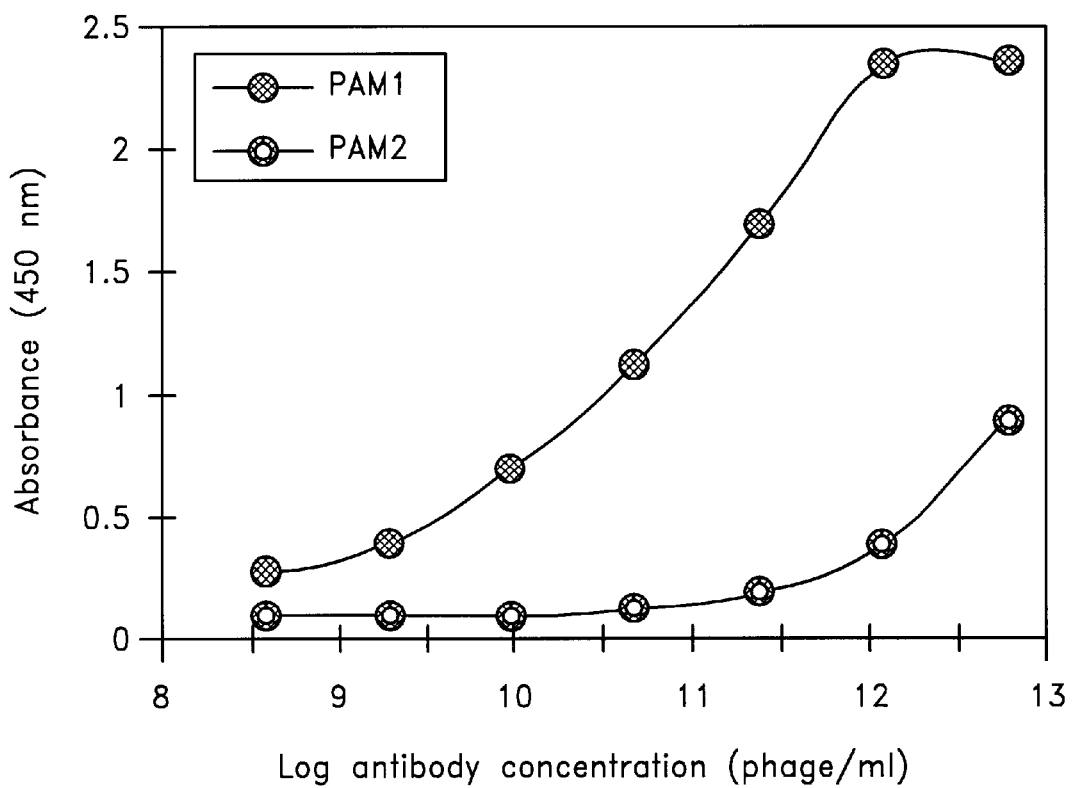
FIG. 1. Relative avidities of the anti-HG-specific phage display antibodies PAM1 and PAM2. Binding of antibodies in an antibody capture ELISA with PGA as the immobilized antigen.

In most cases only results for PAM1 are shown. In additional studies, a control phage monoclonal antibody with specificity directed against maltose binding protein did not bind to any of the pectic or control polysaccharides on immuno-dot-blot-assays or in competitive inhibition ELISAs (see FIG. 1).

EXAMPLE 11

Characterization of de-esterified homogalacturonan specific phage antibodies, PAM1 and PAM2

The specificity of PAM1 for binding to un-esterified and un-substituted HG was determined in immunoassays. In immuno-dot-blot assays, PAM1 bound to PGA and HE81 with detection limits of <1 ng and >1 mg respectively while PAM2 was capable of an approximately 10-fold less sensitive detection of PGA in the same assay. De-esterification of HE81 by sodium carbonate treatment resulted in a decrease in the PAM1 detection limit from the pre-treatment level of >1 mg to a level of <1 ng. PAM1 did not bind at the highest level tested (10 μg) to polymannuronic acid or polyguluronic acid and only bound very weakly to 1 mg of acetylated HG (degree of acetylation 49%, DE 14%). PAM1 bound to a purified de-esterified HG with an average degree of polymerization (DP) of approximately 70, with a detection limit of <1ng. An anti-(1r4)-(-D-galactan antibody (LM5, Jones et al., 1997 Plant Aphysiol. 113, 1405–1412) and an anti-(1r5)-a-L-arabinan (LM6, Willats et al., 1998 Carbohydrate Research 308, 149–152) did not bind to high levels (10 mg) of the same sample, suggesting that no side chains were present on the HG sample.

Figure 2A:
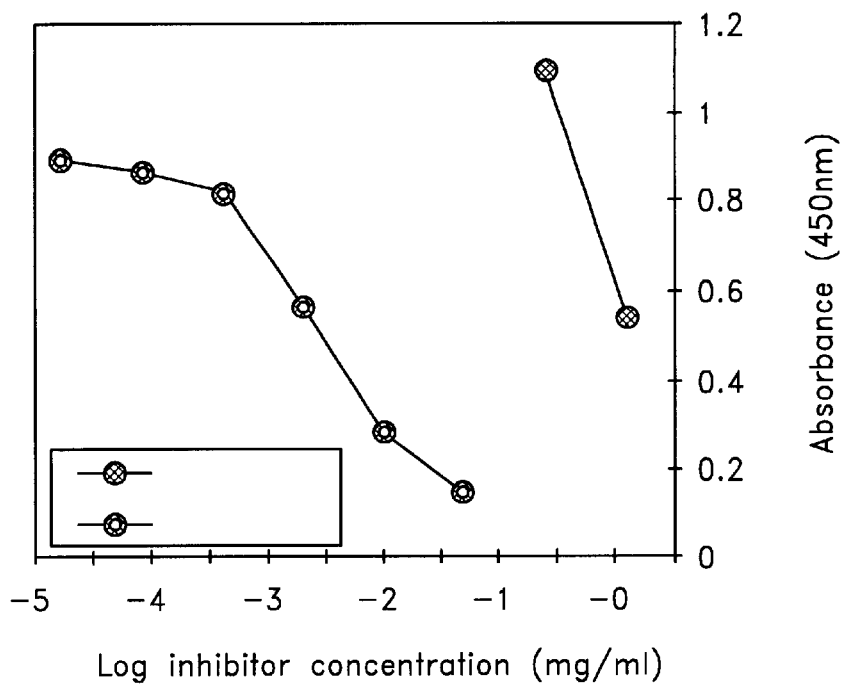
FIG. 2. PAM1 binding to OGAs.

In competitive inhibition ELISAs, in which PGA was the immobilized antigen, an inhibitory concentration (IC50) of 1.5 μg/ml of PGA was required for 50% inhibition of PAM1 binding as shown in Table 1 and FIG. 2A, while HE81, RGI, RGII, xylogalacturonan, polymannuronic acid, polyguluronic failed to inhibit at 1 mg/ml. It was not possible to establish affinities for PAM1 and PAM2 since all the antigens bearing the PAM1 and PAM2 epitopes (such as PGA and HG) are heterogeneous with respect to molecular weight.

TABLE 1

Competitive inhibition ELISA analysis of the binding of PAM1 to pectins with a range of degrees of esterification (DE) prepared with plant (pPME) or fungal (fPME) pectin methyl esterases

|  | DE (%) | IC50 μg/ml[a] |
|---|---|---|
| pPME | 70 | >1000 |
|  | 66 | 603 |
|  | 60 | 115 |
|  | 53 | 45 |
|  | 46 | 19 |
|  | 41 | 1.2 |
| fPME | 76 | >1000 |
|  | 31 | >1000 |
| PGA | 0 | 1.5 |

[a]IC50 values are the concentrations of pectin required to produce 50% inhibition of PAM1 binding to immobilized PGA.

Immunoblotting and competitive inhibition ELISAs with a series of model pectins with defined degrees of esterification were used to characterize PAM1 binding further. The pectins were prepared with pectin methyl esterase (PME) derived from either plants (pPME) or fungi (fPME). There was a strong inverse correlation between PAM1 binding and DE for the pectin samples de-esterified with pPME, with both immuno-dot-blot-assays and competitive inhibition ELISAs, as shown in Table 1. However, PAM1 bound very weakly to fPME treated samples even when the DE was low. For example, on immuno-dot-blots, PAM1 bound to pPME treated pectin with a DE of 46% with a detection limit of <10 ng but to fPME treated pectin with a DE of 43% with a detection limit of >1 mg. In competitive inhibition ELISAs, an fPME treated pectin with a DE of 31% failed to produce significant inhibition at 1 mg/ml (Table 1). These results strongly indicate that the PAM1 epitope is produced by the blockwise action of pPME, but not by the random action of fPME on stretches of methyl esterified HG within pectin molecules, and therefore the PAM1 epitope is a long stretch of contiguous de-esterified GalA residues. The PAM1 binding specificity can therefore be described as de-esterified HG block specific. This binding specificity is desirable/advantageous—in some cases highly desirable/advantageous—as it provides a means for the ready determination as to whether a pectin is suitable for, for example, a particular food, especially a food that benefits from the presence of a block-wise de-esterified pectin.

Immuno-dot-blot analysis of the binding of PAM1 to pectins with a range of Des was performed. High ester pectin samples incubated with pectin methyl esterase from plants (PPME) or fungi (fPME) which de-esterify in a blockwise and random fashion respectively. Samples were dotted onto the nitrocellulose and probed with the anti-pectin antibodies PAM1, JIM5 (anti-galacturonan)(Knox et al. 1997 Int. Rev. Cytol. 171, 79–120) and LM5 (anti-(1r4)-(-D-galactan). In contrast to PAM1, the binding of the monoclonal antibody JIM5, that recognizes low ester pectins, was not strongly correlated to DE. JIM5 was capable of binding to short stretches of contiguous GalA residues (such as those produced by the random action of fPME) and therefore, unlike PAM1, is not de-esterified HG block specific. In order to confirm that the DE did not affect the binding of pectins to nitrocellulose (and therefore produce false negatives) the same pPME and fPME samples were also probed with LM5, the binding of which is independent of DE.

EXAMPLE 12

Characterization of the size of the PAM1 de-esterified HG epitope

Figure 2B:
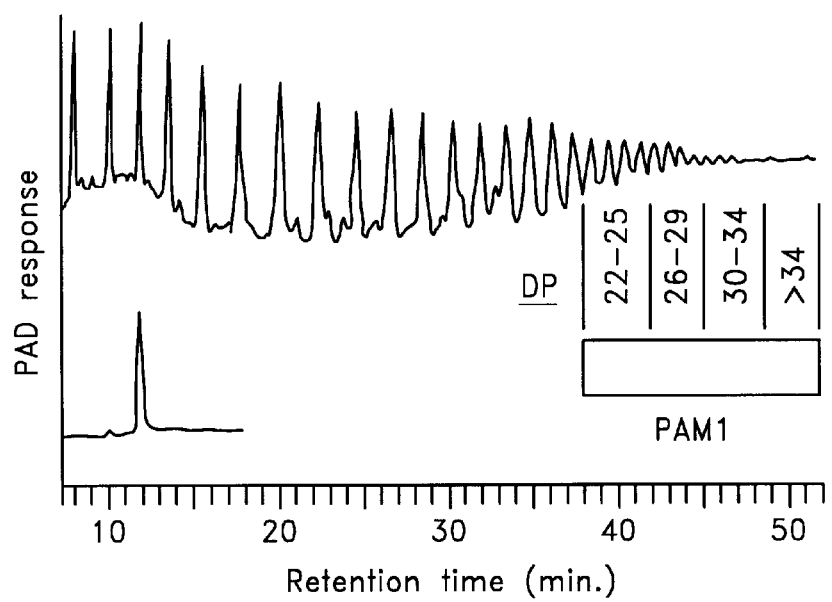

The minimum degree of polymerization (DP) of de-esterified GalA residues required for PAM1 binding was assessed using oligogalacturonide (OGA) samples with a range of DPs used in competitive inhibition ELISAs. Samples with high levels of purity (65%–99%) were only available for OGAs with a DP from 1 to 9. None of the samples in this range inhibited PAM1 binding to immobilized PGA at the highest concentration used of 1 mg/ml. Samples with higher DPs were only available in sufficient amounts for competitive inhibition ELISAs as mixtures enriched with OGAs of known DPs. An IC50 value of 998 mg/ml was obtained for a sample containing OGAs of DPs 13 (7%), 14 (10%) 15 (16%) and 16 (10%) as shown in FIG. 2A. Mixtures that were enriched in OGAs with DPs less than 13 failed to produce 50% inhibition, even at the highest concentration used (1.25 mg/ml), while an IC50 value of 1.5 (g/ml was obtained for PGA (FIG. 2A). Further evidence that PAM1 binding required a large stretch of de-esterified GalA residues was obtained by analysis of fractions obtained from a HPAEC-PAD separation of autoclaved PGA in which a range of OGAs was resolved and those with DPs up to 34 could be identified as shown in FIG. 2B. Pooled fractions containing OGA mixtures were probed with PAM1 by immuno-dot-blotting. PAM1 did not bind to fraction pools containing OGAs with DPs less than 30, bound weakly to a fraction pool containing OGAs with DPs between 30 and 34, and strongly to a pool containing OGAs with DPs >34, as shown in FIG. 2B. The combined evidence suggests that for the most efficient binding to HG, PAM1 requires in the region of 30 contiguous de-esterified residues of GalA.

EXAMPLE 13

Calcium promotes, but is not essential for, PAM1 binding to HG

In competitive inhibition ELISAs, PAM1 bound to pectin in the absence of added calcium but the binding was enhanced by the addition of calcium. A calcium concentration of 0.2 mM resulted in an approximately ten-fold increase in the effectiveness of a pPME prepared pectin with a DE of 41% (P41) as a soluble antigen. A calcium concentration of 1 mM produced no significant further increase in binding. Higher levels of calcium resulted in pectate gel formation and the assays were no longer possible. The addition of magnesium at similar concentrations had no effect. The addition of the calcium chelator CDTA up to 20 $\mu$M had no effect on PAM1 interaction with P41. Essentially identical results were obtained with PGA as the soluble competitor (see FIG. 3).

EXAMPLE 14

Localization of de-esterified HG blocks in plant cells with PAM1 with indirect immunofluorescence microscopy PAM1 was used to immunolocalize de-esterified HG blocks in plant tissues using a three stage detection system involving secondary (anti-M13, produced in mouse) and tertiary (anti-mouse/FITC) antibodies. PAM1 binding to resin-embedded cotyledons of Arabidopsis thaliana either untreated or de-esterified by treatment with sodium carbonate was evaluated. On untreated tissue, PAM1 labelled most intensely at points of direct cell to cell contact and especially at cell junctions. PAM1 labelling was absent from regions of epidermal cell walls that do not adjoin neighboring cells. On de-esterified sections, PAM1 labelled with approximately equal intensity throughout all cell walls.

PAM1 binding to resin-embedded A. thaliana suspension-cultured cells either untreated or de-esterified by treatment with sodium carbonate was evaluated. On untreated sections, PAM1 labelling was fragmentary and disperse while on de-esterified tissue all cells walls were labelled with approximately equal intensity.

PAM1 and JIM5 labelling of whole fixed A. thaliana suspension-cultured cells was evaluated. PAM1 labelling was only present at regions close to direct cell to cell contact at the surface of cell clumps while regions of cell wall without neighbors were unlabeled. In contrast, JIM5 labelled the entire surface of cell clumps, including unadhered regions of cell walls.

In sections of resin-embedded cotyledons of Arabidopsis thaliana PAM1 labelling indicated that de-esterified HG blocks were restricted to certain regions of the cell walls, mostly close to intercellular spaces at cell junctions. Labelling was absent or very weak in regions of cell walls that did not adjoin neighboring cells, for example at the margin of the cotyledon. Chemical de-esterification of sections with sodium carbonate treatment prior to probing with PAM1 extended the labelling to all regions of all primary cell walls. A similar restricted pattern of HG block distribution was seen in untreated sections of A. thaliana suspension-cultured cells, while on de-esterified sections, labelling was intense in all cell walls. With intact, fixed A. thaliana suspension-cultured cells PAM1 labelling was intense at the surface of cell clusters close to cell to cell contacts but was absent from the regions of the surface of cell clusters where cells had no neighbors. In contrast, immunolabelling of A. thaliana suspension-cultured cells with JIM5 revealed that the short de-esterified HG stretches that comprise the JIM5 epitope were distributed evenly across cell clumps, including the unadhered cell walls.

Long stretches of de-esterified HG are produced during tomato fruit ripening by the action of PME and PAM1 labelling was intense throughout all cell walls of resin embedded tomato pericarp that had not been chemically de-esterified.

EXAMPLE 15

PAM1 and PAM2 incorporate antibody variable regions from different VH families

In order to investigate the molecular basis of the differences in binding avidity between PAM1 and PAM2, the scFv genes from both antibodies were sequenced. The scFv antibody fragments of PAM1 and PAM2 consist of single chain peptides as shown in FIGS. 4A and 4B. Each scFv contains a heavy and a light chain fragment separated by a glycine-rich spacer (FIGS. 4A and 4B). Diversity is created in the Synthetic scFv Library (#1) by rearrangement of VH genes while VL genes are identical throughout the entire library. Variability within the heavy chain is derived from the presence of fifty different VH regions within the Synthetic scFv (#1) library in which the CDR3 loops have been replaced by a random sequence of 4–12 amino acid residues. Alignments of the nucleotide sequences of PAM1 and PAM2 to their closest germline counterparts in the VBASE germline directory (Internet website:www.mrc-cpe.cam.ac.uk/imt-doc/restricted/ok.html) using the DNAPLOT alignment package (Internet website:www.mrc-cpe.cam.ac.uk/imt-doc/restricted/ DNAPLOT.html) established that the PAM1 scFv incorporates a V segment encoding CDR1 and CDR2 from the VH3 family which is identical to V segment DP-38 (EMBL citation Z12338) except that the terminal two threonines in FR3 of DP-38 are replaced by alanine and arginine due to the oligonucleotide used to amplify the VH domains during the construction of the Synthetic scFv Library (#1). The PAM2 scFv uses a V segment derived from the the VH4 family which is identical to V segment DP-68 (EMBL citation Z12368) except that in DP-68 the terminal alanine of FR3 is encoded by GCG in DP-68 and by GCA in the PAM2 scFv for the same reason as described above (FIG. 4B). No alignments were found for the segment of random sequence encoding CDR3 which in both PAM1 and PAM2 consists of 7 amino acids. Compared with PAM2, the VH portion of the PAM1 scFv contains 7 more basic residues, 3 more acidic residues and 5 more non-polar residues but 13 less uncharged residues (FIG. 4B).

EXAMPLE 16

Phage display antibodies as analytical tools

Further analysis of enzymatically degraded pectins with the anti-de-esterified homogalacturonan antibody PAM1 has confirmed that phage display antibodies are potentially powerful tools for elucidating pectin structure. Because of the high avidity of the current panel of anti-pectin antibodies it has been possible to rapidly analyze fractions of degraded pectin, often directly and without concentration of the samples.

Complete pectin lyase digestion of P41 did not significantly affect PAM1 binding, whereas PAM1 binding was greatly reduced following PGII digestion. These results further confirm that the PAM1 epitope contains a de-esterified block structure.

EXAMPLE 17

CONCLUSION

We have isolated high avidity phage display antibodies from a naive combinatorial antibody phage library specific to long stretches or blocks of de-esterified HG. To our knowledge this is the first report of the selection of phage display antibodies with specificity against plant cell wall antigens using such a 'single pot' approach. Because immunization and library construction were by-passed, the time taken to generate antibodies was greatly reduced compared with that typical for conventional hybridoma antibodies or a phage display approach involving the generation of an antigen-specific library. Furthermore, carbohydrates are known to generally have low immunogenicity which may be enhanced by coupling to protein. However, since using this approach there was no requirement for the target antigen to be immunogenic, the production of neoglycoproteins was also avoided.

PAM1 is specific to both un-substituted and de-esterified HG and is one of the most highly defined anti-pectin monoclonal antibodies generated. Two monoclonal antibodies have previously been described that bind specifically to de-esterified HG. The monoclonal antibody 2F4 has a minimum binding requirement of nine GalA residues, and has a critical requirement for calcium, indicating that the epitope is probably a calcium cross linked multimer (Liners et al., 1992 Plant Physiology 99, 1099–1104). The epitope of the monoclonal antibody JIM5 is not defined precisely but its epitope involves only a small number of de-esterified GalA residues as it binds to relatively high ester pectins and pectins de-esterified by fPME. The IC50 value for PAM1 binding to a mixture containing OGAs with DPs up to at least 16 was approximately 750-fold greater than the IC50 obtained for PGA, indicating that this mixture did not contain the optimal PAM 1 epitope. Immuno-dot-blot analysis of OGAs fractionated by HPAEC-PAD indicated that the optimal DP is in the region of 30 contiguous GalA residues. This is a considerably larger epitope than that generally thought to be the case for carbohydrates which is in the region of 3 to 6 monosaccharide residues. One possibility is that the PAM1 scFv may recognize a particular conformation of HG that requires a DP of in the region of 30. Such a conformation is unlikely to be the calcium dependent 'egg box' multimers that are known to form between de-esterified HG blocks, since PAM1 binds in the absence of calcium.

Phage antibody populations produced by using helper phage that encode the same coat protein as that which forms the scFv/coat protein fusion product are heterogeneous with respect to valency because of competition for incorporation of the pIII coat proteins into the phage particle (Winter et al., 1994). Such populations are generally considered monovalent since it is estimated that there is an average of less than one fusion peptide displayed per phage particle. Therefore, PAM1 binding is probably mediated by the interaction of single scFvs with the epitope. The interaction may include ionic bonding but is clearly based on more than charge alone since PAM1 and PAM2 did not cross reactive with linear polysaccharides with similar charges to PGA. However, the greater avidity of PAM1 compared to PAM2 may be correlated to the greater number of basic and acidic residues in the PAM1 scFv.

The formation of HG blocks by the action of PME is an important control point in the regulation of the structural properties of cell walls as block formation presages both the assembly of calcium pectate gels and the disassembly of the pectic backbone by the creation of polygalacturonase (PG) cleavage sites. HG blocks and supramolecular HG block multimers cross linked with calcium play an important role in cell adhesion. On untreated cotyledons of A. thaliana, PAM1 bound most intensely at cell junctions, while binding was absent or weak on cell walls that were not adhered to neighboring cells. Similarly, PAM1 binding was absent from non-adhered regions of cell wall in clumps of suspension cultured A. thaliana cells. Moreover, PAM1 bound strongly to untreated sections of ripe tomato pericarp, which is known to contain high levels of de-esterified HG blocks which are formed by the action of PME as fruit ripen and provide substrates for the PG activity that results in progressive disassembly of the pectic network. These results indicate that PAM1 is an effective probe not only for the determination of the distribution of de-esterifed HG blocks in muro but also for the analysis the processes involved in HG block formation and turnover. With the easy access to its scFv gene and protein sequence, the PAM1 probe will be useful to directly address questions of HG block function within the cell wall matrix. The use of synthetic scFv phage display antibodies has several major advantages over conventional monoclonal antibody production. As demonstrated here, the diversity within naive phage display libraries permits the identification of novel antibodies with distinct epitope specificity without the need for immunization. Moreover, the accessibility of the antibody sequence for detailed molecular characterization and the possibility of her manipulation of antibody specificity via protein engineering further strengthen the advantages of this system. Analysis of the VH chain and CDR loop amino acids sequence of PAM1 and PAM2 indicate that despite displaying the same specificity, these two antibodies are derived from completely independent VH and CDR3 sequence rearrangements. Diversity within the Synthetic scFv Library (#1) is derived from the random assembly of 50 different VH family sequences with synthetic random CDR3 loops. The synthetic CDR3 loops within the library range from 4–12 amino acid residues, interestingly both PAM1 and PAM2 contain seven amino acids residues in CDR3 loops that do not share any sequence similarity. In addition, the presence of different VH family regions encoding the CDR1 and CDR2 loops indicate that antibodies of the same discrete specificity can be generated by the combination of distinct VH chain components. The possibility now exists for the synthesis of chimeric antibodies in which the CDR3 loops are exchanged between different VH chain domains. Such rearrangements, coupled to site directed mutagenesis, may yield antibodies of similar specificity but greater avidity, as well as antibodies of subtly altered antigen specificity. The availability of the genes encoding PAM1 and PAM2 also provide the opportunity to express these antibodies in plants with the objective of defining the functions of de-esterified HG blocks during plant development. General teachings on the preparation of transformed plants that are applicable to generate these transformed plants of the present invention may be found in PCT/IB98/00886.

Thus, the present invention provides plant cell wall antibodies without the prior need to have immunized animals. The antibodies of the present invention are anti-homogalacturonan antibodies from a naive phage display library. They may be used to identify de-esterified homogalacturonan blocks in primary cell walls.

In particular, phage display antibodies with specificity for long de-esterified stretches ('blocks') of pectic HG have been isolated from a naive phage display library without the need for prior immunization or conjugation to protein. These antibodies, designated PAM1 and PAM2, bind specifically to de-esterified and un-substituted HG. Assays of antibody binding to a series of pectins de-esterified by the action of plant or fungal pectin methyl esterases indicated that the antibodies were specific to de-esterified HG blocks resulting from the blockwise action of plant pectin methyl esterases. Analysis of antibody binding to a series of oligogalacturonides indicated that PAM1 required in the region of 30 de-esterified GalA residues for optimal binding. PAM1 has been used to identify and locate HG block structures formed in primary cell walls by the action of plant pectin methyl esterases.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

By way of example, the antibody of the present invention may be used in combination with one or more other antibodies than can also recognize certain —but different— motifs on a pectin structure.

What is claimed is:

1. An isolated antibody capable of binding de-esterified homogalacturonan, wherein the antibody comprises the amino acid sequence of SEQ ID NO:1, or fragment thereof wherein said fragment is capable of binding de-esterified homogalacturonan.

2. An isolated antibody capable of binding de-esterified homogalacturonan, wherein the antibody comprises the amino acid sequence of SEQ ID NO:3, or fragment thereof wherein said fragment is capable of binding de-esterified homogalacturonan.

3. An antibody conjugate comprising the antibody according to claims 1, 2 wherein the antibody is linked to a detectable moiety.

4. A kit comprising an antibody according to claim 3 and reagents for identifying the detectable moiety.

* * * * *